United States Patent [19]

Fukushima et al.

[11] Patent Number: 5,317,159
[45] Date of Patent: May 31, 1994

[54] METHOD OF USING AN ELECTRON CAPTURE TYPE DETECTOR

[75] Inventors: Toyoaki Fukushima, Kyoto; Shozo Tanabe, Osaka, both of Japan

[73] Assignee: Shimadzu Corporation, Kyoto, Japan

[21] Appl. No.: 979,828

[22] Filed: Nov. 20, 1992

[30] Foreign Application Priority Data

Jan. 31, 1992 [JP] Japan .................................. 4-46145

[51] Int. Cl.$^5$ .............................................. G01T 1/185
[52] U.S. Cl. ...................................... 250/381; 250/379
[58] Field of Search ............... 250/379, 380, 384, 381; 324/469

[56] References Cited

U.S. PATENT DOCUMENTS 4,445,037 4/1984 Anderson ........................... 250/379

FOREIGN PATENT DOCUMENTS 1-146158 10/1989 Japan .................................. 250/379
2042253 9/1980 United Kingdom ................ 250/384

Primary Examiner—Carolyn E. Fields
Attorney, Agent, or Firm—Heller, Ehrman, White & McAuliffe

[57] ABSTRACT

An electron capture type detector for gas chromatography has an ionization vessel containing therein line sources for a radioactive isotope serving as a negative electrode, a collector electrode, a purge gas route, a discharge gas route, and an end of a column disposed at its lower section. The collector electrode includes a filament made of a heat resistant material and itself connected to a heating device such that the filament can be heated to about 300°-600° C. so as to eliminate contaminants deposited on the collector electrode by thermal decomposition, oxidation or reduction, without the necessity of disassembling the detector itself. The contaminants are effectively removed by simultaneously causing air or hydrogen gas to pass over the collector electrode through the ionization vessel from the purge gas route to the discharge gas route.

2 Claims, 1 Drawing Sheet

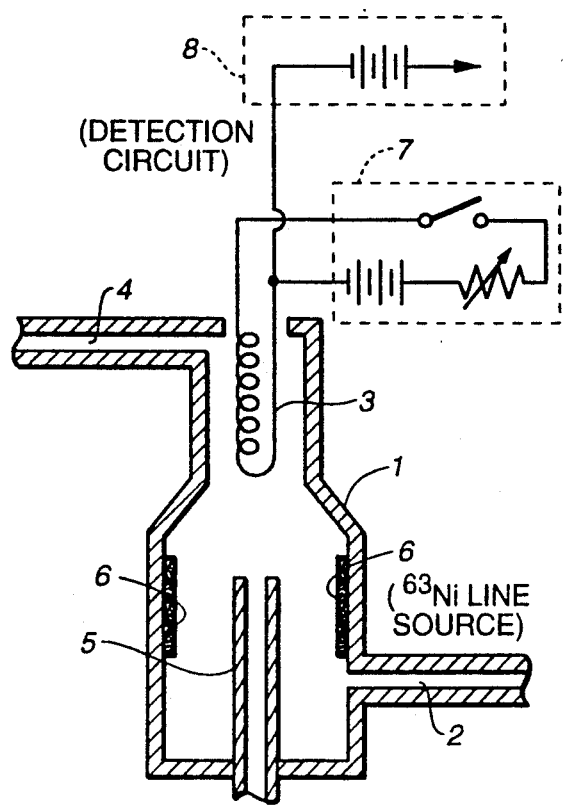
FIG._1
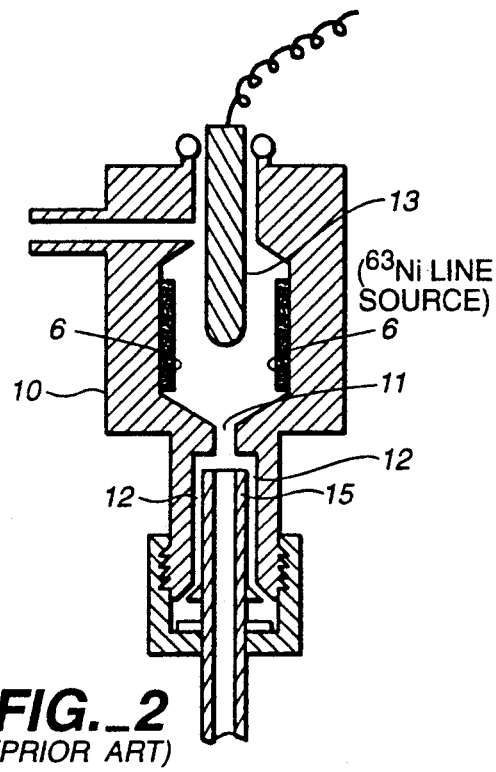
FIG._2
(PRIOR ART)
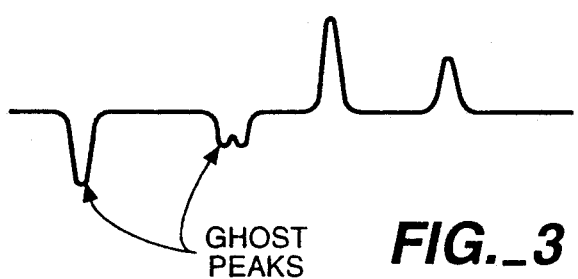
FIG._3

METHOD OF USING AN ELECTRON CAPTURE TYPE DETECTOR

BACKGROUND OF THE INVENTION

This invention relates to a method of using a detector for gas chromatography. In particular, this invention relates a method of using to a detector of the electron capture type suited for the detection of substances containing a compound with electron affinity.

Electron capture type detectors, which are a kind of detectors for gas chromatography, are suited for the analysis of halogen and nitro compounds and are used for the detection of residual organic mercury, agricultural chemicals or PCB, as well as small amounts of steroid and amino acids as derivatives with electron affinity.

As shown in FIG. 2, a prior art detector of the electron capture type has a small ionization vessel 10 enclosing therein line sources 6 of a radioactive isotope such as $^{63}$Ni serving as negative electrodes and an end part of a column 15 positioned at a bottom section of the vessel 10 to form a nozzle 11 such that a sample, flowing out through this end part of the column 15, can be sent upward within the vessel 10. According to the exemplary design shown in FIG. 2, a pure nitrogen gas can be introduced through purge gas intake routes 12 onto the surfaces of the line sources 6 such that the nitrogen gas thus introduced into the vessel 10 and the $\beta$-rays from the line sources 6 generate electrons above the nozzle 11. The electrons thus generated are attracted by an electrostatic field towards a positive collector electrode 13 disposed at an upper part of the vessel 10 and caused to collide with the sample flowing our from the column 15 at the outlet of the nozzle 11, thereby generating negative ions if the sample contains substances with electron affinity. Such negative ions are attracted by and move in the electric field towards the collector electrode 13 but, since these ions move more slowly than the electrons, they have the effect of interfering with the steady flow of current to the collector electrode 13. The detector is designed so as to record the changes in voltage necessary for keeping the current flowing into the collector electrode 13 at a constant rate and to thereby generate a signal indicative of (or proportional to) the concentration of the negative ions.

Prior art electron capture type detectors, as described above, have been in use as highly sensitive and selective detectors with respect to compounds with electron affinity. In order to maintain stability over a long period of time of use, however, they must be cleaned because they become contaminated by the column liquid phase or the components of the samples. Japanese Utility Model Publication Jikkai 1-146158 disclosed an electron capture type detector which allows its interior to be cleaned. Although contamination of an electron capture type detector takes place mainly on the collector electrode and the line sources, contamination of the collector electrode presents a more serious problem in the case of cleanable electron capture type detectors.

When an electron capture type detector is contaminated, its detection sensitivity becomes adversely affected or ghost peaks appear in the chromatograph as shown in FIG. 3, preventing accurate detection. If a radioactive isotope such as $^{63}$Ni is used as line sources 6, furthermore, its handling may be subject to governmental regulations, and specialized knowledge would be required for taking out internal components for cleaning. In other words, one cannot freely disassemble such a detector to clean its internal components.

SUMMARY OF THE INVENTION

In view of the above, it is an object of the present invention to provide an electron capture type detector which can be cleaned without disassembling it when its collector electrode has become contaminated and a method of operating such a detector such that it will have an extended useful lifetime.

An electron capture type detector embodying the present invention, with which the above and other objects can be accomplished, may be characterized not only as comprising an ionization vessel enclosing therein line sources of a radioactive isotope serving as negative electrodes, a collector electrode, purge gas routes, and a gas discharge route and having an end part of a column positioned at a bottom part of the ionization vessel, but also wherein the collector electrode comprises a filament made of a heat-resistant material and itself connected to a heating means. Such a detector is effectively cleaned by heating the collector electrode to remove the contaminants therefrom and simultaneously causing air or hydrogen gas to pass thereover through the ionization chamber vessel from the purge gas route to the discharge gas route.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a schematic sectional view of a principal portion of an electron capture type detector embodying the present invention;

FIG. 2 is a schematic sectional view of a principal portion of a prior art electron capture type detector; and FIG. 3 is an example of chromatogram with the appearance of ghost peaks.

DETAILED DESCRIPTION OF THE INVENTION

FIG. 1 shows an electron capture type detector embodying the present invention, comprising an ionization vessel 1 of a small volume, a collector electrode 3, purge gas routes 2, and a discharge gas route 4, having an end part of a column 5 positioned at a lower section of the interior of the ionization vessel 1. Line sources 6 of a radioactive isotope such as $^{63}$Ni are sealed as negative electrodes on the inner walls of the ionization vessel 1.

The collector electrode 3 is disposed at an upper section of the ionization vessel 1 and comprises a filament made of a heat-resistant material such as platinum (Pt) or nickel (Ni) and connected to an electrically heating means 7 so as to allow itself to be thereby heated. Since this heating means 7 is for the purpose of cleaning the collector electrode 3, when the latter has become contaminated with the sample, etc., by eliminating such contaminating substances, the heating means 7 is designed such that the collector electrode 3 can be heated adjustably to a temperature in the range of about 300°-600° C. This range of temperature is selected because contaminants deposited on the collector electrode 3 can be removed by thermal decomposition, oxidation or reduction in this temperature range. Accordingly, the collector electrode 3 of the present invention is required to be heat-resistant to the extent of withstanding heating to this temperature range.

The heating means 7 can be switched both on and off. Since the collector electrode 3 needs to be heated by the heating means 7 only when it is contaminated with contaminants, the heating means 7 is normally in the condition of being switched off. The collector electrode 3 is also connected to a detection circuit 8 for detecting sample components, as explained above with reference to the prior art detector.

In using the detector thus structured, a purge gas such as nitrogen is caused to pass through the purge gas routes 2, causing electrons to be generated within the ionization vessel 1 by the nitrogen gas thus introduced thereinto and the $\beta$-rays from the line sources 6. The electrons thus generated are attracted towards the positive collector electrode 3 above by the force of an electrostatic field and collide with the sample flowing out of the column 5, forming negative ions if the sample contains any substance with electron affinity. Since these negative ions move more slowly than the electrons, they have the effect of interfering with the steady flow of current to the collector electrode 3, as was the case with the prior art detector explained above.

When the collector electrode 3 has become contaminated with a liquid phase or samples flowing out from the column 5 and it is desired to clean it, a carrier gas is allowed to continue flowing in through the column 5 and the heating means 7 is switched on such that the temperature is adjusted to a desired level. If the carrier gas is switched to air or hydrogen ($H_2$), the contaminants deposited on the collector electrode 3 can be eliminated by undergoing thermal decomposition, oxidation or reduction, whereby the collector electrode 3 is cleaned and the sensitivity of the detector is restored to the original condition before the contamination, allowing normal response to be obtainable. Thus, detector can be used with samples which tend to contaminate the collector electrode or under conditions where contamination is likely to occur.

In summary, a detector according to the present invention does not have to be disassembled in order to have its collector cleaned. In other words, the cleaning of the collector electrode, which used to be a cumbersome process, can be carried out while the detector is kept in the normal assembled condition, and the useful lifetime of the collector electrode can be thereby extended.

What is claimed is:

1. A method of operating an electron capture type detector, said detector comprising an ionization vessel having therein line sources for a radioactive isotope serving as a negative electrode, a collector electrode, a purge gas route and a discharge gas route, and having an end of a column disposed at a lower section of said ionization vessel, said method comprising the steps of:

heating said collector electrode, for removing contaminants from said collector electrode, by causing an electric current to flow through a filament which is connected to a heating means and of which said collector electrode is comprised; and simultaneously causing air or hydrogen gas to pass through said ionization vessel from said purge gas route to said discharge gas route over said collector electrode.

2. The method of claim 1 wherein said filament is heated to a temperature in the range of about 300°–600° C.

* * * * *